(12) United States Patent
Baker, Jr.

(10) Patent No.: US 8,640,699 B2
(45) Date of Patent: Feb. 4, 2014

(54) BREATHING ASSISTANCE SYSTEMS WITH LUNG RECRUITMENT MANEUVERS

(75) Inventor: Clark R. Baker, Jr., Newman, CA (US)

(73) Assignee: Covidien LP, Mansfield, MA (US)

( * ) Notice: Subject to any disclaimer, the term of this patent is extended or adjusted under 35 U.S.C. 154(b) by 1009 days.

(21) Appl. No.: 12/409,406

(22) Filed: Mar. 23, 2009

(65) Prior Publication Data
US 2009/0241957 A1    Oct. 1, 2009

Related U.S. Application Data

(60) Provisional application No. 61/040,092, filed on Mar. 27, 2008.

(51) Int. Cl.
F16K 31/02    (2006.01)
A61M 16/00    (2006.01)
A62B 7/00    (2006.01)

(52) U.S. Cl.
USPC ............. 128/204.23; 128/204.18; 128/204.21

(58) Field of Classification Search
USPC ............. 128/200.24, 204.18, 204.23, 204.21, 128/204.22, 205.12
See application file for complete search history.

(56) References Cited

U.S. PATENT DOCUMENTS

| | | | |
|---|---|---|---|
| 2,008,009 A | 7/1935 | Firestone | |
| 3,961,627 A | 6/1976 | Ernst et al. | |
| 4,036,221 A | 7/1977 | Hillsman et al. | 128/145.6 |
| 4,889,116 A | 12/1989 | Taube | 128/204.23 |
| 5,072,729 A | 12/1991 | DeVries | 128/204.23 |
| 5,094,235 A | 3/1992 | Westenskow et al. | 128/204.22 |
| 5,103,814 A | 4/1992 | Maher | 128/204.18 |
| 5,129,390 A | 7/1992 | Chopin et al. | 128/204.21 |
| 5,303,698 A | 4/1994 | Tobia et al. | 128/204.21 |
| 5,315,989 A | 5/1994 | Tobia | 128/204.28 |
| 5,320,093 A | 6/1994 | Raemer | 128/203.12 |
| 5,335,654 A | 8/1994 | Rapoport | |
| 5,365,922 A | 11/1994 | Raemer | 128/204.23 |
| 5,388,575 A | 2/1995 | Taube | 128/204.23 |
| 5,402,796 A | 4/1995 | Packer et al. | 128/719 |
| 5,429,123 A | 7/1995 | Shaffer et al. | |

(Continued)

FOREIGN PATENT DOCUMENTS

| | | | | |
|---|---|---|---|---|
| EP | 0504725 A3 | 9/1992 | ............. | A61B 5/083 |
| EP | 0615764 B | 5/1999 | ............ | A61M 16/00 |

(Continued)

OTHER PUBLICATIONS

Nellcor Symphony N-3000 Pulse Oximeter Home Use Guide, Nellcor Puritan Bennett Inc., 90 pages, 1996.

(Continued)

*Primary Examiner* — Lynne Anderson
*Assistant Examiner* — Bradley Philips

(57) ABSTRACT

The disclosure provides a method for controlling the delivery of a breathing gas to a patient including automatic lung recruitment maneuvers. The method may include regulating the $FiO_2$ and the PEEP of the breathing gas delivered to the patient, determining a blood oxygenation level of the patient, automatically adjusting the $FiO_2$ of the breathing gas delivered to the patient based on at least the blood oxygenation level of the patient, and in response to determining that the $FiO_2$ of the breathing gas delivered to the patient exceeds a pre-determined value: automatically initiating a lung recruitment maneuver; and automatically increasing the PEEP of the breathing gas delivered to the patient.

20 Claims, 3 Drawing Sheets

(56) References Cited

U.S. PATENT DOCUMENTS

| | | |
|---|---|---|
| 5,490,502 A | 2/1996 | Rapoport et al. |
| 5,492,109 A | 2/1996 | Hirschl et al. ............ 128/201.21 |
| 5,520,192 A | 5/1996 | Kitney et al. |
| 5,540,220 A | 7/1996 | Gropper et al. |
| 5,575,283 A | 11/1996 | Sjoestrand |
| 5,598,838 A | 2/1997 | Servidio et al. |
| 5,645,053 A | 7/1997 | Remmers et al. ......... 128/204.23 |
| 5,660,170 A | 8/1997 | Rajan et al. |
| 5,669,379 A | 9/1997 | Somerson et al. |
| 5,678,539 A | 10/1997 | Schubert et al. |
| 5,682,877 A | 11/1997 | Mondry ................. 128/204.23 |
| 5,715,415 A | 2/1998 | Dazey et al. |
| 5,738,090 A | 4/1998 | Lachmann et al. |
| 5,752,509 A | 5/1998 | Lachmann et al. |
| 5,803,066 A | 9/1998 | Rapoport et al. |
| 5,813,399 A | 9/1998 | Isaza et al. ............... 128/204.21 |
| 5,881,723 A | 3/1999 | Wallace |
| 5,915,379 A | 6/1999 | Wallace |
| 5,915,380 A | 6/1999 | Wallace |
| 5,921,920 A | 7/1999 | Marshall et al. |
| 5,927,274 A | 7/1999 | Servidio et al. |
| 5,931,160 A | 8/1999 | Gilmore et al. |
| 5,937,854 A | 8/1999 | Stenzler |
| 5,957,129 A | 9/1999 | Tham et al. |
| 5,964,220 A | 10/1999 | Boussignac et al. |
| 6,024,089 A | 2/2000 | Wallace |
| 6,067,022 A | 5/2000 | Laswick et al. |
| 6,116,241 A | 9/2000 | Huygen et al. |
| 6,142,149 A | 11/2000 | Steen ..................... 128/204.23 |
| 6,148,814 A | 11/2000 | Clemmer et al. ......... 128/200.24 |
| 6,158,430 A | 12/2000 | Pfeiffer et al. |
| 6,158,432 A | 12/2000 | Biondi et al. ............ 128/204.21 |
| 6,165,151 A | 12/2000 | Weiner ........................ 604/66 |
| 6,192,876 B1 | 2/2001 | Denyer et al. |
| 6,206,001 B1 | 3/2001 | Garber et al. |
| 6,206,837 B1 | 3/2001 | Brugnoli |
| 6,240,920 B1 | 6/2001 | Strom |
| 6,269,812 B1 | 8/2001 | Wallace |
| 6,273,088 B1 | 8/2001 | Hillsman |
| 6,286,508 B1 | 9/2001 | Remmers et al. ......... 128/204.18 |
| 6,305,372 B1 | 10/2001 | Servidio |
| 6,305,373 B1 | 10/2001 | Wallace |
| 6,322,502 B1 | 11/2001 | Schoenberg et al. |
| 6,360,745 B1 | 3/2002 | Wallace et al. |
| 6,369,838 B1 | 4/2002 | Wallace et al. |
| 6,390,091 B1 | 5/2002 | Banner et al. ............ 128/204.21 |
| 6,390,092 B1 | 5/2002 | Leenhoven |
| 6,398,728 B1 | 6/2002 | Bardy |
| 6,435,182 B1 | 8/2002 | Lutchen et al. |
| 6,439,229 B1 | 8/2002 | Du et al. ................. 128/204.23 |
| 6,463,930 B2 | 10/2002 | Biondi et al. |
| 6,488,029 B1 | 12/2002 | Toth et al. ...................... 128/845 |
| 6,512,938 B2 | 1/2003 | Claure et al. .................. 600/323 |
| 6,532,957 B2 | 3/2003 | Berthon-Jones |
| 6,533,730 B2 | 3/2003 | Ström |
| 6,551,243 B2 | 4/2003 | Bocionek et al. |
| 6,557,553 B1 | 5/2003 | Borrello ................. 128/204.18 |
| 6,561,187 B2 | 5/2003 | Schmidt et al. .......... 128/204.23 |
| 6,564,797 B1 | 5/2003 | Mechlenburg et al. |
| 6,569,095 B2 | 5/2003 | Eggers |
| 6,575,163 B1 | 6/2003 | Berthon-Jones |
| 6,584,973 B1 | 7/2003 | Biondi et al. |
| 6,631,716 B1 | 10/2003 | Robinson et al. ......... 128/204.21 |
| 6,644,312 B2 | 11/2003 | Berthon-Jones et al. 128/204.23 |
| 6,651,657 B1 | 11/2003 | Manigel et al. |
| 6,668,829 B2 | 12/2003 | Biondi et al. |
| 6,671,529 B2 | 12/2003 | Claure et al. .................. 600/325 |
| 6,675,801 B2 | 1/2004 | Wallace et al. |
| 6,688,307 B2 | 2/2004 | Berthon-Jones |
| 6,709,405 B2 | 3/2004 | Jonson |
| 6,717,589 B1 | 4/2004 | Grillo et al. |
| 6,718,975 B2 | 4/2004 | Blomberg |
| 6,743,172 B1 | 6/2004 | Blike |
| 6,745,764 B2 | 6/2004 | Hickle |
| 6,752,150 B1 | 6/2004 | Remmers et al. |
| 6,761,165 B2 | 7/2004 | Strickland, Jr. .......... 128/204.22 |
| 6,796,305 B1 | 9/2004 | Banner et al. |
| 6,804,656 B1 | 10/2004 | Rosenfeld et al. |
| 6,807,965 B1 | 10/2004 | Hickle |
| 6,810,876 B2 | 11/2004 | Berthon-Jones |
| 6,832,609 B2 | 12/2004 | Wright et al. |
| 6,840,241 B2 | 1/2005 | Ström |
| 6,845,773 B2 | 1/2005 | Berthon-Jones et al. |
| 6,860,266 B2 | 3/2005 | Blike |
| 6,899,103 B1 | 5/2005 | Hood et al. ................... 128/845 |
| 6,920,875 B1 | 7/2005 | Hill et al. |
| 6,920,878 B2 | 7/2005 | Sinderby et al. |
| 6,986,347 B2 | 1/2006 | Hickle |
| 7,011,091 B2 | 3/2006 | Hill et al. |
| 7,017,574 B2 | 3/2006 | Biondi et al. |
| 7,018,341 B2 | 3/2006 | Wright et al. |
| 7,036,504 B2 | 5/2006 | Wallace |
| 7,046,254 B2 | 5/2006 | Brown et al. |
| 7,051,735 B2 | 5/2006 | Mechlenburg et al. |
| 7,066,173 B2 | 6/2006 | Banner et al. |
| 7,073,501 B2 | 7/2006 | Remmers et al. |
| 7,074,196 B2 | 7/2006 | Kück et al. |
| 7,081,091 B2 | 7/2006 | Merrett et al. |
| 7,086,399 B2 | 8/2006 | Makinson et al. |
| 7,089,937 B2 | 8/2006 | Berthon-Jones et al. |
| 7,100,607 B2 | 9/2006 | Zdrojkowski et al. |
| 7,117,438 B2 | 10/2006 | Wallace et al. |
| 7,121,277 B2 | 10/2006 | Ström |
| 7,137,389 B2 | 11/2006 | Berthon-Jones |
| 7,201,734 B2 | 4/2007 | Hickle |
| 7,207,945 B2 | 4/2007 | Bardy |
| 7,210,478 B2 | 5/2007 | Banner et al. |
| 7,246,618 B2 | 7/2007 | Habashi |
| 7,247,154 B2 | 7/2007 | Hickle |
| 7,256,708 B2 | 8/2007 | Rosenfeld et al. |
| 7,258,670 B2 | 8/2007 | Bardy |
| 7,270,126 B2 | 9/2007 | Wallace et al. |
| 7,296,573 B2 | 11/2007 | Estes et al. |
| 7,307,543 B2 | 12/2007 | Rosenfeld et al. |
| 7,308,894 B2 | 12/2007 | Hickle |
| 7,315,825 B2 | 1/2008 | Rosenfeld et al. |
| 7,321,862 B2 | 1/2008 | Rosenfeld et al. |
| 7,322,937 B2 | 1/2008 | Blomberg et al. |
| 7,334,578 B2 | 2/2008 | Biondi et al. |
| 7,346,846 B2 | 3/2008 | Rossi, Jr. et al. |
| 7,374,535 B2 | 5/2008 | Schoenberg et al. |
| 7,395,216 B2 | 7/2008 | Rosenfeld et al. |
| 7,433,827 B2 | 10/2008 | Rosenfeld et al. |
| 7,454,359 B2 | 11/2008 | Rosenfeld et al. |
| 7,454,360 B2 | 11/2008 | Rosenfeld et al. |
| 7,467,094 B2 | 12/2008 | Rosenfeld et al. |
| 7,475,019 B2 | 1/2009 | Rosenfeld et al. |
| 7,520,279 B2 | 4/2009 | Berthon-Jones |
| 7,556,038 B2 | 7/2009 | Kirby et al. |
| 7,561,912 B2 | 7/2009 | Schatz et al. |
| 7,562,657 B2 | 7/2009 | Blanch et al. |
| 7,565,905 B2 | 7/2009 | Hickle |
| 7,650,291 B2 | 1/2010 | Rosenfeld et al. |
| 7,681,571 B2 | 3/2010 | Makinson et al. |
| 7,698,156 B2 | 4/2010 | Martucci et al. |
| 7,708,015 B2 | 5/2010 | Seeger et al. |
| 7,717,112 B2 | 5/2010 | Sun et al. |
| 7,778,851 B2 | 8/2010 | Schoenberg et al. |
| 7,831,450 B2 | 11/2010 | Schoenberg et al. |
| 7,886,231 B2 | 2/2011 | Hopermann et al. |
| 2002/0023640 A1 | 2/2002 | Nightengale ............ 128/200.24 |
| 2002/0026941 A1 | 3/2002 | Biondi et al. |
| 2002/0078957 A1 | 6/2002 | Remmers et al. ......... 128/204.18 |
| 2002/0177758 A1 | 11/2002 | Schoenberg et al. |
| 2002/0195105 A1 | 12/2002 | Blue et al. ............... 128/204.21 |
| 2003/0029452 A1 | 2/2003 | Suki et al. |
| 2003/0106553 A1 | 6/2003 | Vanderveen |
| 2003/0111078 A1* | 6/2003 | Habashi ................... 128/204.18 |
| 2003/0140928 A1 | 7/2003 | Bui et al. |
| 2003/0141981 A1 | 7/2003 | Bui et al. |
| 2003/0145852 A1 | 8/2003 | Schmidt et al. ........... 128/203.12 |
| 2003/0153818 A1 | 8/2003 | Bocionek et al. |
| 2003/0188748 A1 | 10/2003 | Sinderby et al. .......... 128/204.21 |
| 2003/0213488 A1 | 11/2003 | Remmers et al. ......... 128/204.18 |

(56) References Cited

U.S. PATENT DOCUMENTS

| | | | |
|---|---|---|---|
| 2003/0230308 A1 | 12/2003 | Linden | |
| 2004/0003813 A1 | 1/2004 | Banner et al. | 128/204.21 |
| 2004/0041828 A1 | 3/2004 | Zellhoefer | |
| 2004/0050387 A1 | 3/2004 | Younes | 128/204.18 |
| 2004/0074497 A1 | 4/2004 | Berthon-Jones et al. | 128/204.23 |
| 2004/0097821 A1 | 5/2004 | Blomberg et al. | |
| 2004/0121767 A1 | 6/2004 | Simpson et al. | |
| 2004/0159323 A1 | 8/2004 | Schmidt et al. | 128/204.23 |
| 2004/0167804 A1 | 8/2004 | Simpson et al. | |
| 2004/0172302 A1 | 9/2004 | Martucci et al. | |
| 2004/0236240 A1 | 11/2004 | Kraus et al. | |
| 2004/0244807 A1 | 12/2004 | Sun et al. | |
| 2005/0016534 A1 | 1/2005 | Ost | |
| 2005/0039127 A1 | 2/2005 | Davis | |
| 2005/0043969 A1 | 2/2005 | Sarel | |
| 2005/0055242 A1 | 3/2005 | Bello et al. | |
| 2005/0065817 A1 | 3/2005 | Mihai et al. | |
| 2005/0109340 A1 | 5/2005 | Tehrani | 128/204.21 |
| 2005/0112325 A1 | 5/2005 | Hickle | |
| 2005/0115564 A1 | 6/2005 | DeVries et al. | 128/204.18 |
| 2005/0124866 A1 | 6/2005 | Elaz | |
| 2005/0133024 A1 | 6/2005 | Coifman | |
| 2005/0150494 A1 | 7/2005 | DeVries et al. | 128/204.21 |
| 2005/0204310 A1 | 9/2005 | De Zwart et al. | |
| 2006/0011200 A1 | 1/2006 | Remmers et al. | 128/204.23 |
| 2006/0037616 A1 | 2/2006 | Seeger et al. | |
| 2006/0085229 A9 | 4/2006 | Rosenfeld et al. | |
| 2006/0089543 A1 | 4/2006 | Kim et al. | |
| 2006/0112959 A1 | 6/2006 | Mechlenburg et al. | |
| 2006/0135878 A1 | 6/2006 | Wright et al. | |
| 2006/0201505 A1 | 9/2006 | Remmers et al. | |
| 2006/0211950 A1 | 9/2006 | Brunner et al. | |
| 2006/0213519 A1 | 9/2006 | Schmidt et al. | |
| 2006/0237015 A1 | 10/2006 | Berthon-Jones et al. | |
| 2006/0249149 A1 | 11/2006 | Meier et al. | |
| 2006/0249151 A1 | 11/2006 | Gambone | |
| 2006/0260611 A1 | 11/2006 | Garber et al. | |
| 2006/0271409 A1 | 11/2006 | Rosenfeld et al. | |
| 2006/0276701 A1 | 12/2006 | Ray | |
| 2006/0294464 A1 | 12/2006 | Tokimoto et al. | |
| 2007/0000494 A1 | 1/2007 | Banner et al. | |
| 2007/0017515 A1 | 1/2007 | Wallace | |
| 2007/0028921 A1 | 2/2007 | Banner et al. | |
| 2007/0050715 A1 | 3/2007 | Behar | |
| 2007/0062528 A1 | 3/2007 | Heinonen et al. | |
| 2007/0062529 A1 | 3/2007 | Choncholas et al. | |
| 2007/0062533 A1 | 3/2007 | Choncholas et al. | |
| 2007/0068528 A1 | 3/2007 | Bohm et al. | |
| 2007/0089741 A1* | 4/2007 | Bohm et al. | 128/203.12 |
| 2007/0093721 A1 | 4/2007 | Lynn et al. | |
| 2007/0144517 A1 | 6/2007 | Foster et al. | |
| 2007/0149860 A1 | 6/2007 | Lynn et al. | |
| 2007/0163579 A1 | 7/2007 | Li et al. | |
| 2007/0173702 A1 | 7/2007 | Dlugos et al. | |
| 2007/0199566 A1 | 8/2007 | Be'eri | |
| 2007/0203415 A1 | 8/2007 | Bardy | |
| 2007/0203422 A1 | 8/2007 | Bardy | |
| 2007/0203423 A1 | 8/2007 | Bardy | |
| 2007/0213658 A1 | 9/2007 | Hickle | |
| 2007/0232867 A1 | 10/2007 | Hansmann | |
| 2007/0240717 A1 | 10/2007 | Kaczka et al. | |
| 2008/0000479 A1 | 1/2008 | Elaz et al. | |
| 2008/0021379 A1 | 1/2008 | Hickle | |
| 2008/0041380 A1 | 2/2008 | Wallace | |
| 2008/0066752 A1 | 3/2008 | Baker et al. | |
| 2008/0072900 A1 | 3/2008 | Kenyon et al. | |
| 2008/0072901 A1 | 3/2008 | Habashi | 128/204.18 |
| 2008/0091117 A1 | 4/2008 | Choncholas et al. | |
| 2008/0092043 A1 | 4/2008 | Trethewey | |
| 2008/0110460 A1 | 5/2008 | Elaz et al. | |
| 2008/0230065 A1 | 9/2008 | Heinonen | |
| 2008/0236582 A1 | 10/2008 | Tehrani | |
| 2008/0295839 A1* | 12/2008 | Habashi | 128/204.22 |
| 2008/0314385 A1 | 12/2008 | Brunner et al. | |
| 2009/0020120 A1 | 1/2009 | Schatzl et al. | |
| 2009/0143694 A1 | 6/2009 | Krauss et al. | |
| 2009/0149723 A1 | 6/2009 | Krauss et al. | |
| 2009/0241956 A1 | 10/2009 | Baker, Jr. | |
| 2009/0241957 A1 | 10/2009 | Baker, Jr. | A61M 16/00 |
| 2009/0241958 A1 | 10/2009 | Baker, Jr. | A61M 16/00 |
| 2009/0270752 A1 | 10/2009 | Coifman | |
| 2009/0275811 A1 | 11/2009 | Schatz et al. | |
| 2009/0293877 A1 | 12/2009 | Blanch et al. | |
| 2009/0314290 A1 | 12/2009 | Hickle | |
| 2010/0030091 A1 | 2/2010 | Fine | |
| 2010/0037895 A1 | 2/2010 | Berthon-Jones et al. | |
| 2010/0108064 A1 | 5/2010 | Blackwell et al. | |
| 2010/0192094 A1 | 7/2010 | Jeha et al. | |
| 2010/0199015 A1 | 8/2010 | Martucci et al. | |
| 2010/0292544 A1 | 11/2010 | Sherman et al. | |
| 2011/0004489 A1 | 1/2011 | Schoenberg et al. | |
| 2011/0023881 A1 | 2/2011 | Thiessen | |

FOREIGN PATENT DOCUMENTS

| | | | |
|---|---|---|---|
| EP | 0549685 B | 12/1999 | A61M 16/00 |
| EP | 540024 B1 | 2/2000 | A61M 16/10 |
| EP | 0998318 B1 | 5/2000 | A61M 16/00 |
| EP | 1132106 A2 | 9/2001 | A61M 16/00 |
| EP | 0671181 B1 | 5/2002 | A61M 16/00 |
| EP | 1189649 B1 | 6/2005 | A61M 16/00 |
| EP | 1579883 A2 | 9/2005 | A61M 16/00 |
| EP | 1586344 A2 | 10/2005 | A61M 16/00 |
| GB | 1565916 A | 4/1980 | |
| GB | 1581482 A | 12/1980 | |
| WO | 92/04865 | 4/1992 | A61B 5/08 |
| WO | 92/11052 | 7/1992 | A61M 15/00 |
| WO | 93/09834 | 5/1993 | A61M 16/00 |
| WO | WO 95/16484 | 6/1995 | |
| WO | WO 98/29790 | 7/1998 | |
| WO | WO 98/41267 | 9/1998 | |
| WO | WO 98/41269 | 9/1998 | |
| WO | WO 98/41270 | 9/1998 | |
| WO | WO 98/41271 | 9/1998 | |
| WO | WO 98/53732 | 12/1998 | |
| WO | 99/04841 | 2/1999 | A61M 16/00 |
| WO | 99/62399 | 12/1999 | A61B 5/00 |
| WO | WO 99/62403 | 12/1999 | |
| WO | 00/18460 | 4/2000 | A61M 16/00 |
| WO | 00/45702 | 8/2000 | A61B 5/08 |
| WO | 00/45702 A1 | 8/2000 | A61M 16/00 |
| WO | 00/45880 | 8/2000 | A61M 16/00 |
| WO | 00/45880 A1 | 8/2000 | A61M 16/00 |
| WO | WO 00/45882 | 8/2000 | |
| WO | WO 00/79466 | 12/2000 | |
| WO | 01/00264 A1 | 1/2001 | A61M 16/00 |
| WO | 01/00265 A1 | 1/2001 | A61M 16/00 |
| WO | 02/47741 A2 | 6/2002 | |
| WO | 02/47741 A3 | 6/2002 | A61B 5/00 |
| WO | WO 02/45566 | 6/2002 | |
| WO | WO 02/095200 | 11/2002 | |
| WO | WO 03/053503 | 7/2003 | |
| WO | WO 03/102850 | 12/2003 | |
| WO | 2004/002561 A2 | 1/2004 | A61M 16/00 |
| WO | 2004/002561 A3 | 1/2004 | A61M 16/00 |
| WO | WO 2004/030509 | 4/2004 | |
| WO | 2004/071591 A1 | 8/2004 | A63B 22/00 |
| WO | WO 2004/069095 | 8/2004 | |
| WO | WO 2004/070546 | 8/2004 | |
| WO | WO 2004/070548 | 8/2004 | |
| WO | WO 2004/070549 | 8/2004 | |
| WO | WO 2004/070556 | 8/2004 | |
| WO | WO 2004/070557 | 8/2004 | |
| WO | WO 2004/070562 | 8/2004 | |
| WO | WO 2004/070994 | 8/2004 | |
| WO | WO 2004/070995 | 8/2004 | |
| WO | 2004/073482 A2 | 9/2004 | |
| WO | WO 2004/082751 | 9/2004 | |
| WO | 2005/051280 A2 | 6/2005 | |
| WO | WO 2005/050525 | 6/2005 | |
| WO | WO 2005/051177 | 6/2005 | |
| WO | 2005/102432 | 11/2005 | A61M 16/01 |
| WO | WO2005102432 | 11/2005 | |
| WO | 2006/005432 A1 | 1/2006 | A61M 16/00 |

(56) References Cited

FOREIGN PATENT DOCUMENTS

| WO | WO 2006/012205 | 2/2006 | | |
|---|---|---|---|---|
| WO | WO 2007/050435 | 5/2007 | | |
| WO | WO 2007/085110 | 8/2007 | | |
| WO | WO 2007145948 | 12/2007 | | |
| WO | WO 2008/021222 | 2/2008 | | |
| WO | 2008/148134 | 12/2008 | ............ | A61M 16/00 |
| WO | WO 2008/154430 A | 12/2008 | | |
| WO | WO2008148134 | 12/2008 | | |
| WO | WO 2010/011928 | 1/2010 | | |

OTHER PUBLICATIONS

7200 Series Ventilator, Options, and Accessories: Operator's Manual. Nellcor Puritan Bennett, Part No. 22300 A, Sep. 1990, pp. 1-196. (196 page), Sep. 1990.

7200 Ventilatory System: Addendum/Errata. Nellcor Puritan Bennett, Part No. 4-023576-00, Rev. A, Apr. 1988, pp. 1-32. (32 pages), Apr. 1998.

800 Operator's and Technical Reference Manual. Series Ventilator System, Nellcor Puritan Bennett, Part No. 4-070088-00, Rev. L, Aug. 2010, pp. 1-476. (476 pages), Aug. 2010.

840 Operator's and Technical Reference Manual. Ventilator System, Nellcor Puritan Bennett, Part No. 4-075609-00, Rev. G, Oct. 2006, pp. 1-424. (424 pages), Oct. 2006.

International Search Report re: PCT/US09/037985 mailed Sep. 17, 2009.

Tusman et al., G., "Effects of Recruitment Maneuver on Atelectasis in Anesthetized Children", Anesthesiology, American Society of Anesthesiologists, vol. (98)(1), Jan. 1, 2003, pp. 14-22, XP009050788, ISSN: 0003-3022.

U.S. Appl. No. 12/408,546, Office Action mailed Aug. 10, 2012, 10 pgs.

U.S. Appl. No. 12/409,412, Office Action mailed Aug. 29, 2012, 13 pgs.

PCT International Search Report and Written Opinion in International Application PCT/US2009/037857, mailed Jun. 17, 2009, 12 pgs.

U.S. Appl. No. 12/408,546, Office Action mailed Mar. 30, 2012, 11 pgs.

U.S. Appl. No. 12/409,412, Office Action mailed Mar. 30, 2012, 11 pgs.

\* cited by examiner

FIG. 2

BREATHING ASSISTANCE SYSTEMS WITH LUNG RECRUITMENT MANEUVERS

RELATED APPLICATION

This application claims priority from U.S. Patent Application No. 61/040,092 which was filed on Mar. 27, 2008, and is incorporated herein by reference in its entirety.

BACKGROUND

Conventional breathing assistance systems typically include a gas delivery system, a patient interface to deliver gas to one or more breathing passages of the patient, and a connection system between the gas delivery system and the patient interface. Such breathing assistance systems may be used, e.g., for mechanical ventilation of a patient's lungs and/or treatment of an apnea or other medical condition. The gas delivery system may include a controller configured to vary the flow rate, pressure, and/or other characteristics of the gas delivered to the patient, based on the intended treatment or condition of the patient.

Many modern ventilators include sensors operable to measure various parameters regarding the patient's breathing patterns and/or the operation of the ventilator, and may allow the caregiver to adjust ventilator settings to select or adjust the ventilation strategy being implemented. For example, a gas delivery system may sense one or more of the following parameters: airway pressure, exhaled volume, ventilation mode, type of breath, mean airway pressure, peak airway pressure, PEEP/CPAP pressure, plateau pressure, respiratory rate, I:E ratio, tidal volume, minute volume, and spontaneous minute volume.

Clinical treatment of a ventilated patient often requires that physiological characteristics of the patient be monitored to detect the effects of a particular ventilation strategy on a patient or changes in the patient's breathing patterns. Saturation of Peripheral Oxygen ($Sp_{O2}$) is an estimation of the oxygen saturation level in a patient's blood usually measured with a pulse oximeter and is one physiological characteristic that may be used in ventilation control. For example, a gas delivery system may control the fraction of inspired oxygen ($FiO_2$) in the gas delivered based on the $Sp_{O2}$ measured. One embodiment employing this example includes a controller that may adjust the $FiO_2$ by an amount proportional to the difference between a measured $Sp_{O2}$ and a user-specified target $Sp_{O2}$.

SUMMARY

In accordance with one embodiment of the present disclosure, method for controlling the delivery of a breathing gas to a patient may include: regulating the fractional inspired oxygen ($FiO_2$) and the positive end expiratory pressure (PEEP) of the breathing gas delivered to the patient; determining a blood oxygenation level of the patient; automatically adjusting the $FiO_2$ of the breathing gas delivered to the patient based on the blood oxygenation level of the patient; and in response to determining that the $FiO_2$ of the breathing gas delivered to the patient exceeds a pre-determined value: automatically initiating a lung recruitment maneuver; and automatically increasing the PEEP of the breathing gas delivered to the patient subsequent to the completion of the lung recruitment maneuver.

In accordance with another embodiment of the present disclosure, a breathing assistance system configured to deliver a breathing gas toward a patient may include: a gas delivery control system configured to regulate the fractional inspired oxygen ($FiO_2$) and the positive end expiratory pressure (PEEP) of the breathing gas delivered to the patient; a parameter module configured to determine a blood oxygenation level of the patient; wherein the gas delivery control system automatically adjusts the $FiO_2$ of the breathing gas delivered to the patient based at least on the blood oxygenation level of the patient; wherein the gas delivery control system automatically initiates a lung recruitment maneuver when the $FiO_2$ of the breathing gas exceeds a pre-determined value; and wherein the gas delivery control system automatically increases the PEEP of the breathing gas delivered to the patient subsequent to performing the lung recruitment maneuver.

In accordance with another embodiment of the present disclosure, a computer-readable storage medium may store a set of instructions executable on a processor. The set of instructions may include: instructions for regulating the fractional inspired oxygen ($FiO_2$) and the positive end expiratory pressure (PEEP) of the breathing gas delivered to the patient; instructions for determining a blood oxygenation level of the patient; instructions for automatically adjusting the $FiO_2$ of the breathing gas delivered to the patient based on the blood oxygenation level of the patient; and in response to determining that the $FiO_2$ of the breathing gas delivered to the patient exceeds a pre-determined value: instructions for automatically initiating a lung recruitment maneuver; and instructions for automatically increasing the PEEP of the breathing gas delivered to the patient subsequent to the completion of the lung recruitment maneuver.

In accordance with another embodiment of the present disclosure, a breathing assistance system may include: means for regulating the fractional inspired oxygen ($FiO_2$) and the positive end expiratory pressure (PEEP) of the breathing gas delivered to the patient; means for determining a blood oxygenation level of the patient; means for automatically adjusting the $FiO_2$ of the breathing gas delivered to the patient based on the blood oxygenation level of the patient; and in response to determining that the $FiO_2$ of the breathing gas delivered to the patient exceeds a pre-determined value: means for automatically initiating a lung recruitment maneuver; and means for automatically increasing the PEEP of the breathing gas delivered to the patient subsequent to the completion of the lung recruitment maneuver.

BRIEF DESCRIPTION OF THE DRAWINGS

Some embodiments of the disclosure may be understood by referring, in part, to the following description and the accompanying drawings wherein:

FIG. 2 illustrates an example display device displaying a group of ventilation parameters, according to one example embodiment of the present disclosure;

DETAILED DESCRIPTION OF THE DRAWINGS

Figure 1:
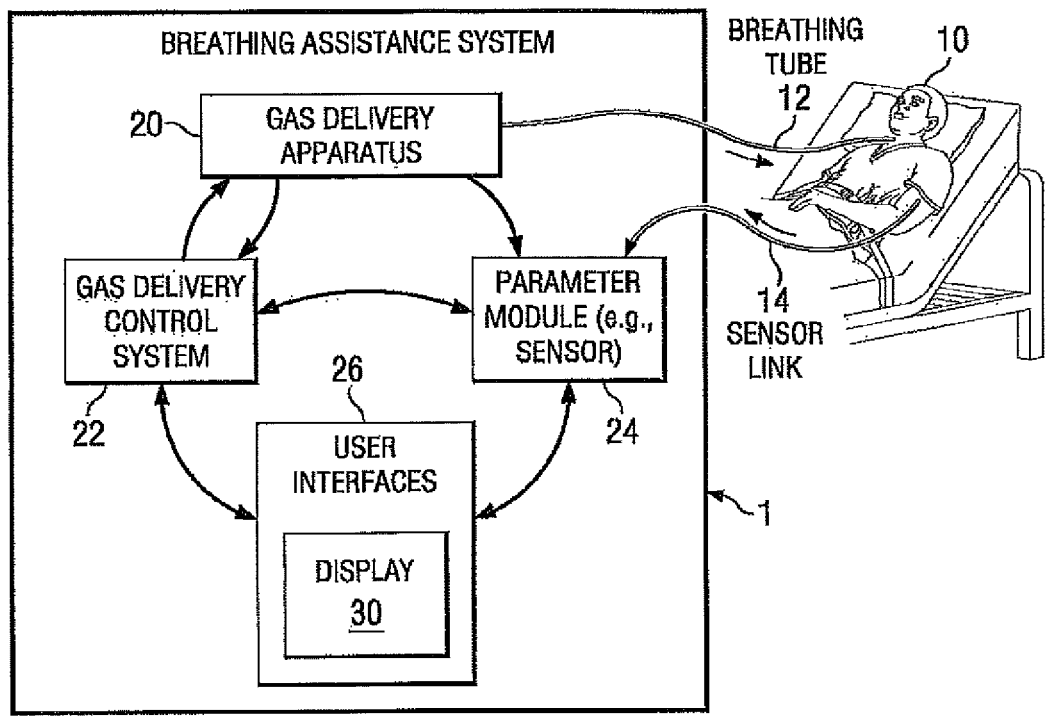
FIG. 1 illustrates an example breathing assistance system, according to one embodiment of the present disclosure.

Selected embodiments of the disclosure may be understood by reference, in part, to FIGS. 1-5, wherein like numbers refer to same and like parts. The present disclosure is broadly concerned with breathing assistance systems (e.g., ventilators, CPAP systems, or BiPAP systems) adapted to provide breathing assistance to a patient (e.g., providing ventilation and/or treating an apnea or other breathing condition).

In some embodiments, the breathing assistance system may control breathing assistance based on two or more ventilation parameters. For example, the breathing assistance system may control $FiO_2$ of the breathing gas delivered based on blood oxygenation level (e.g., $SpO_2$) and one or more other ventilation parameters.

In other embodiments, the breathing assistance system may control breathing assistance based on an adjustable target value for one or more ventilation parameters. For example, the breathing assistance system may control $FiO_2$ of the breathing gas delivered based on a target value for blood oxygenation level and may adjust that target value based on one or more other ventilation parameters.

In yet other embodiments, the breathing assistance system may control breathing assistance including automatically recommending and/or initiating lung recruitment maneuvers. For example, the breathing assistance system may control $FiO_2$ of the breathing gas delivered based on a target value for blood oxygenation level and may recommend a lung recruitment maneuver based on one or more other ventilation parameters.

Ventilation parameters may include any data relevant and/or related to the delivery of breathing gas to a patient. For example, ventilation parameters may include physiological parameters of the patient, medical history of the patient, equipment-related parameters, historical data related to the delivery of breathing gas, and/or user inputs. Physiological parameters of the patient may include any ventilation parameter measured, sensed, and/or related to the patient's condition (e.g., blood oxygenation level (e.g., $SpO_2$), lung compliance, lung resistance, rapid-shallow breathing index (RSBI), patient work of breathing (WOB), pulse rate, blood pressure, temperature, and/or any other indicator of the patient's condition). As examples, some physiological parameters may be sensed by the breathing assistance system and/or gathered from a user.

Medical history of the patient may include any ventilation parameter related to the historical condition of the patient (e.g., age, height, weight, medication, historical blood pressure, previous and/or current disease, and/or any other information that might be used to inform and/or adjust medical treatment of the patient). As examples, ventilation parameters related to a patient's medical history may be gathered from a user, delivered to the breathing assistance system from an information handling system (e.g.) a computer, a doctor's PDA, etc.), and/or received from any other source of information for a patient's medical history.

Equipment-related parameters may include any ventilation parameter related to the operation of the breathing assistance system (e.g., signal quality of a physiological parameter. Positive end-expiratory pressure (PEEP), set PEEP, $PEEP_{HIGH}$, $PEEP_{LOW}$, peak inspiratory pressure, tidal volume, set tidal volume, plateau pressure, frequency, pressure support, volume support, percent support, total work of breathing, airway pressure, exhaled volume, ventilation mode, type of breath, mean airway pressure, peak airway pressure, plateau pressure, respiratory rate, I:E ratio, tidal volume, minute volume, spontaneous minute volume, end expiratory flow, inspiratory time, and/or any other ventilation parameter related to the operation of the breathing assistance system). As examples, equipment-related parameters may include data sensed and/or measured by the breathing assistance system, historical data related to the control and/or operation of the breathing assistance system, and/or any other data related to the operation of the breathing assistance system.

Any one or more ventilation parameters may be displayed on a display device. As examples, a display device may display an instantaneous value for any ventilation parameter, a trace or historical trend for any ventilation parameter, an alarm or alert if the value of a ventilation parameter passes a pre-set or calculated threshold, and/or any other indication related to a ventilation parameter that might be of use to a clinician, the patient, and/or other user of a breathing assistance system.

FIG. 1 illustrates an example breathing assistance system 1 for providing breathing assistance to a patient 10, according to one embodiment of the disclosure. Breathing assistance system 1 may be generally configured to provide breathing assistance to a patient 10 (e.g., to provide ventilation and/or treat an apnea, snoring, or other breathing condition). Breathing assistance system 1 may include a gas delivery apparatus 20, a gas delivery control system 22 for regulating the delivery of breathing gas to patient 10, a parameter module 24 for collecting and/or manipulating data related to ventilation parameter(s), one or more user interfaces 26 for receiving user input, and a display 30 for displaying ventilation parameters and/or other data related to breathing assistance system 1.

Patient 10 may be connected to breathing assistance system 1 by a variety of devices and/or components. For example, breathing gas may be delivered toward a patient through a patient circuit 12. Patient circuit 12 may include tubes, conduits, breathing masks, endotracheal tubes, and/or any other component or device configured for the delivery of gas toward patient 10. As another example, breathing assistance system 1 may receive data related to patient 10 through link 14. In some embodiments, link 14 may be configured to communicate data gathered from patient 10 by one or more sensors (e.g., a pulse-oximeter, a blood-pressure cuff, and/or any other physiologic parameter that might be of use in the treatment of patient 10).

Gas delivery apparatus 20 may include any device or devices configured to generate, supply, and/or deliver gas (e.g., pressurized air) toward patient 10 via a connection system (e.g., a breathing circuit) and/or a patient interface (e.g., a tracheal tube or mask). For example, gas delivery apparatus 20 may comprise a device capable of generating pressurized air (e.g., a ventilator, CPAP system, or BiPAP system), a wall outlet through which pressurized air may be supplied (e.g., in a hospital or clinic), one or more tanks of compressed gas, a compressor, or any other suitable source of pressurized or non-pressurized gas. Gas delivery apparatus 20 may further include any other components suitable for providing functionality related to providing breathing assistance to a patient 10. For example, gas delivery apparatus 20 may include one or more sensors, a humidifier, a nebulizer, an alarm system, and/or any other suitable components.

As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example.

As used herein, the term "patient" may refer to any person or animal that may receive breathing assistance from system 1, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Gas delivery control system 22 may be operable to control the breathing assistance provided by gas delivery apparatus 20 based on various input. For example, gas delivery control system 22 may regulate the pressure and/or flow of gas delivered to patient 10 based on various input received by gas delivery control system 22. Such input may include input received from an operator (e.g., via a touch screen and/or other user interfaces 26), data related to the operation of breathing assistance system 1, and/or data received by parameter module 24 via link 14 (e.g., one or more sensors or other electronic devices). Gas delivery control system 22 may be configured to deliver gas based on any protocol and/or treatment regimen useful in the care of patient 10. For example, gas delivery control system may be configured to perform lung recruitment maneuvers.

Gas delivery control system 22 may include, or have access to, one or more processors, memory devices, and any other suitable hardware or software. The one or more memory devices may store instructions (e.g., any suitable software, algorithms, or other logic or instructions that may be executed by one or more processors) for controlling the operation of gas delivery apparatus 20, e.g., controlling ventilation support provided by gas delivery apparatus 20. As another example, gas delivery control system 22 may include any system or device for executing code or logic instructions (e.g., software or firmware) for controlling user interface 26, e.g., a microcontroller, a digital signal processor (DSP), an application specific integrated controller (ASIC), electrically-programmable read-only memory (EPROM), or a field-programmable gate array (FPGA).

Parameter module 24 may include a sensor, a storage device, and/or any other device or component configured to collect and/or to manipulate data related to one or more ventilation parameters. For example, parameter module 24 may include a storage device to store discrete values for ventilation parameters and/or historical trends of ventilation parameters (e.g., electrically-programmable read-only memory (EPROM), a field-programmable gate array (FPGA), a computer disk, a flash drive, punch cards or any other system suitable for such storage). As another example, parameter module 24 may include one or more sensors configured to collect ventilation parameters, such as sensors associated with patient 10, gas delivery apparatus 20, the surrounding atmosphere, and/or any other data related to patient 10 and/or the operation of gas delivery apparatus 20. As yet another example, parameter module 24 may be configured to receive data from a user via user interface 26 (e.g., a keyboard, a touchpad, and/or any other device described below).

User interface 26 may include any systems or devices allowing a user to input data or otherwise interact with breathing assistance system 1, as well as any systems or devices allowing data output to a user. For example, user interface 26 may include one or more physical interfaces (e.g., physical buttons, knobs, sliders, dials, levers, or switches) provided by breathing assistance system 1. As another example, user interface 26 may be provided by a graphical user interface (GUI), and/or a touch screen display (e.g., on display 30). User interface 26 may be coupled to, integrated with, or otherwise associated with display 30, gas delivery control system 22, and/or gas delivery apparatus 20. As examples, user interface 26 may include electrical interfaces (e.g., a desktop computer, laptop computer, or network terminal), and/or other means of interface (e.g., a wireless control pad or a PDA).

In some embodiments, user interface 26 may be operable to exhibit one or more ventilation parameters. For example, in the case of physical user interfaces (e.g., physical buttons, knobs, sliders, dials, levers, or switches), various identifiers may be written or otherwise displayed on the physical user interfaces. As another example, in the case of a touch screen display, various ventilation parameters may be displayed on the screen.

As discussed above, user interface 26 may include or be associated with display 30 configured to display various information regarding breathing assistance system 1 (e.g., data regarding patient 10, the operation of gas delivery apparatus 20, menus, icons, selection tools and/or any other relevant data). In particular, display 30 may display the ventilation parameters selected by breathing assistance system 1 or by a user for display. Display 30 may indicate a trend for particular ventilation parameters by displaying a plot of each ventilation parameter versus time. Display 30 may indicate one or more ventilation parameters in any other suitable manner to a user (e.g., using any suitable graphics, text, numerical values, colors, or other indications).

Figure 2:
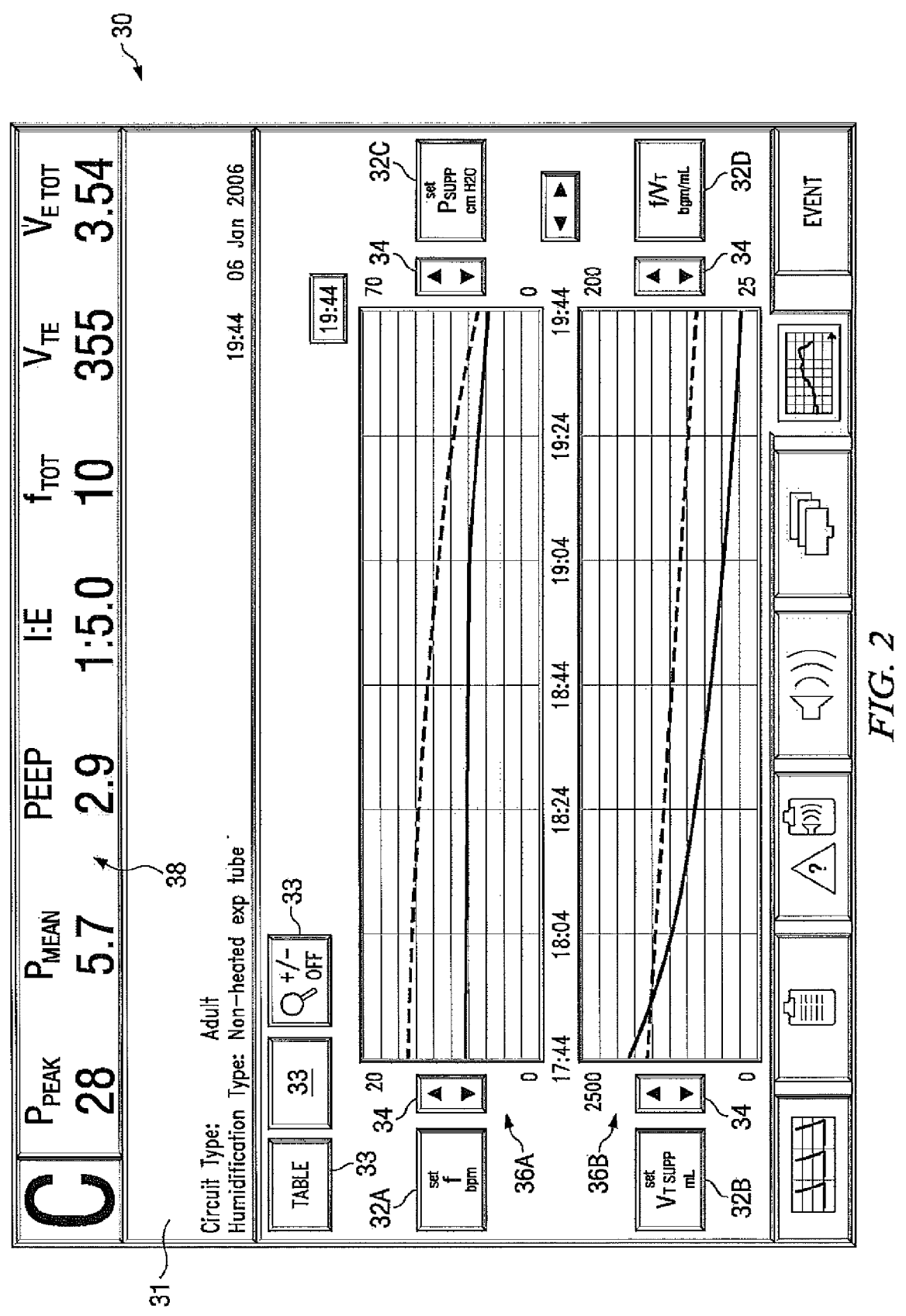

FIG. 2 depicts an example display 30 displaying a group of ventilation parameters, according to one example embodiment of the present disclosure. Display 30 may include any system or device for displaying various information regarding breathing assistance system 1 (e.g., data regarding patient 10, the operation of gas delivery apparatus 20, menus, icons, selection tools and/or any other relevant data). Display 30 may comprise any type of screen or other visual display (e.g., a touch screen display, and/or oscilloscope). Display 30 may be partially or fully integrated with, or may be physically separate from, gas delivery apparatus 20. For example, display 30 may comprise an integrated screen of a ventilator, CPAP, or BiPAP device, or a separate device such as a standalone monitoring device or a laptop computer. As discussed above, display 30 may display various ventilation parameters related to breathing assistance system 1 (e.g., data regarding patient 1, the operation of gas delivery apparatus 20, menus, icons, selection tools, and/or any other relevant data).

The ventilation parameters and/or other data displayed by display 30 may be determined in any suitable manner and based on any suitable data or input. For example, one or more preprogrammed sets of data and/or ventilation parameters may be selected by a user. As another example, in some embodiments, display 30 may be configured and/or modified by a user (e.g., a technician or caregiver). In such embodiments, user interface 26 may allow a user to configure/modify one or more of the ventilation parameters displayed by display 30 (e.g., via a series of menus, prompts, and/or other user input systems).

In the illustrated embodiment, display 30 includes a touch screen GUI display 31 which displays a number of selectable buttons 33, which operate as user interfaces, e.g., for navigating through screens or displays and/or for selecting, configuring, and/or modifying various ventilation parameters regarding breathing assistance system 1. In the illustrated embodiment, a user may use buttons 33 to display and/or select one or more ventilation parameters for display. For example, as shown in FIG. 2, display 30 may display a set of tags 32 that each identify a particular ventilation parameter.

When the user selects a particular ventilation parameter for display (using buttons 33 or other user interface 26), the selected ventilation parameters may be displayed (e.g., simultaneously or otherwise) in display 30. As discussed above, a value for each ventilation parameter may be displayed in any suitable manner to indicate a trend for that ventilation parameter over time, an instantaneous value for the ventilation parameter, and/or any other information related to one or more ventilation parameters.

As one example, display 30 may show an instantaneous value for one or more ventilation parameters in banner 38. As another example, a plot of multiple ventilation parameters over time (e.g., f, $V_{TSUPP}$, $P_{SUPP}$, and $f/V_T$) may be displayed, as shown in charting areas 36A and 36B. In this embodiment, each charting area 32 may be used to display a pair of ventilation parameters (e.g., 32A and 32B). Data for ventilation parameters may be distinguished from each other by color, line type, or in any other manner. In other embodiments, each ventilation parameter may have a separate charting area 32. As shown in FIG. 2, display 30 may also include scale adjusters 34 that may be selected by a user to adjust the scale for the relevant data, e.g., to keep the trend data from moving outside of the relevant charting area (e.g., when a value becomes too low or too high).

Controlling the $FiO_2$ of the Breathing Gas Delivered to the Patient Based on More than One Ventilation Parameter In accordance with certain embodiments of the present disclosure, breathing assistance system 1 may control the fraction of inspired oxygen ($FiO_2$) of the breathing gas delivered to patient 10 based on more than one ventilation parameter. For example, breathing assistance system 1 may primarily control FiO in the delivered breathing gas based on the measured arterial blood oxygenation level (e.g., $SpO_2$ and/or $PaO_2$) and one or more additional ventilation parameters.

The following examples are offered as particular embodiments to illustrate the selection of the one or more additional ventilation parameters and are not intended to be an exhaustive list. For example, breathing assistance system 1 may control $FiO_2$ of the breathing gas delivered to patient 10 based on measured $SpO_2$ and at least one additional physiological parameter (e.g., pulse rate, respiration rate, minute volume, tidal volume, inspiratory pressure, blood pressure, cardiac output, rapid shallow breathing index (RSBI), etc.), In another example, breathing assistance system 1 may use at least one equipment-related parameter (e.g., one or more signal quality parameters associated with the indication of blood oxygenation). In another example, breathing assistance system 1 may use at least one user input. In another example, breathing assistance system 1 may use at least one historical datum stored in parameter module 24 (e.g., the number of previous adjustments to $FiO_2$ in the last thirty minutes). In each example, the data used to control the delivery of breathing gas to patient 10 may be collected by parameter module 24 using link 14 or any other device or component for collecting data.

In accordance with the teachings of the present disclosure, gas delivery control system 22 may combine a measured value of blood oxygenation (e.g., $SpO_2$, and/or $pO_2$) and at least one additional ventilation parameter in any useful manner to control $FiO_2$ of the breathing gas delivered to patient 10. The combination may be any algorithm and/or mathematical function that provides a clinically useful indication related to the delivery of breathing gas to patient 10. For example, gas delivery control system 22 may establish asymmetric criteria for adjusting $FiO_2$ in one direction (e.g., inhibiting any decrease of $FiO_2$ if the patient's pulse rate has deviated from a programmed baseline but allowing increases of $FiO_2$ without regard to the patient's pulse rate). In another embodiment, gas delivery control system 22 may adjust the $FiO_2$ by an amount proportional to the difference between a measured $SpO_2$ and a user-specified target value for $SpO_2$. As a secondary consideration, however, breathing assistance system 1 may consider the prior adjustment of $FiO_2$ and delay adjusting $FiO_2$ a second time until some time has passed (e.g., $FiO_2$ can only be changed once in five minutes). Although the following paragraphs offer specific examples of such control schemes, they are not exhaustive. Persons having ordinary skill in the art will be able to use the teachings of the present disclosure to their advantage in other specific embodiments.

In some embodiments, gas delivery control system 22 may adjust $FiO_2$ with a goal of maintaining a target value of blood oxygenation for patient 10. Using teachings of the present disclosure, gas delivery control system 22 may adjust the target value of oxygenation based on one or more additional ventilation parameters. For example, gas delivery control system 22 may primarily adjust $FiO_2$ in order to match measured $SpO_2$ to a target $SpO_2$ value (e.g., a target $SpO_2$ value set by a clinician) and secondarily adjust the target $SpO_2$ value in response to a change in one or more additional ventilation parameters. For example, gas delivery control system 22 may reduce the target $SpO_2$ value if the patient's blood pressure reduces below a defined threshold value. In another example, gas delivery control system 22 may increase the target $SpO_2$ value if the patient's pulse rate increases above a defined threshold value.

Gas delivery control system 22 may change the magnitude, interval, and/or response time of such adjustment based on one or more additional ventilation parameters. In another example, gas delivery control system 22 may inhibit the adjustment of the target $SpO_2$ value based on one or more ventilation parameters related to the condition of the equipment used for $FiO_2$ control or delivery (e.g., gas delivery apparatus 20 and gas delivery control system 22). For example, gas delivery control system 22 may delay the adjustment of $FiO_2$ if the supply of oxygen for use by gas delivery control system 22 is below a certain threshold value and/or is being replaced.

In some embodiments, gas delivery control system 22 may be configured to provide a user alert and/or another indication to a user and/or clinician. For example, some criteria for an alert may include the $FiO_2$ of the delivered breathing gas, the measured value of blood oxygenation, and one or more additional ventilation parameters. For example, gas delivery control system 22 may be configured to provide an alert if adjustment of $FiO_2$ of the breathing gas delivered to patient 10 has been inhibited due to the value of a second ventilation parameter (e.g., pulse rate). As another example, gas delivery control system 22 may be configured to provide an alert if the $FiO_2$ of the breathing gas increases above a defined threshold without an accompanying increase in measured $SpO_2$ (e.g., an alert for possible change in the condition of the patient's lungs).

Gas delivery control system 22 may be configured to provide an audible alarm, a visual warning (e.g., a flashing light or a text display), and/or a tactile indicator, using display 30 and/or user interface 26. Additional examples include embodiments using display 30 as shown in FIG. 2. Ventilation parameters displayed in charting area 36 may include an alert level or line (e.g., showing an upper or lower limit). Charting area 36 may include a vertical demarcation indicating specific times when an adjustment has been made. Display 30 may also show a trace or trend of adjustments to $FiO_2$ over time along with any data that underlie the adjustments.

As a specific embodiment, gas delivery control system 22 may inhibit decreases in $FiO_2$ of the breathing gas delivered to patient 10 when any of the following conditions is true: (a) $FiO_2$ of the breathing gas delivered to patient 10 has already dropped by a predetermined amount within a predetermined time (e.g., 5 percent in the last 5 minutes); (b) status information from a pulse oximeter indicates that the underlying oximetry signal may be of poor quality (e.g., the oximeter's Pulse Search indication is set); or (c) the current pulse rate, respiration rate, and minute volume have changed by a predetermined amount from a previously measured baseline.

In another specific embodiment, gas delivery control system 22 may be configured to inhibit any adjustments in $FiO_2$ of the breathing gas delivered to patient 10 if any of the following conditions is true: (a) an oximetry signal is not available; (b) the ventilator cannot supply the requested $FiO_2$ of the breathing gas delivered to patient 10 (e.g.) there is a loss of gas pressure in the supply lines, or the patient circuit is occluded or disconnected); or (c) the user has provided an override (e.g., selected a specific $FiO_2$ of the breathing gas delivered to patient 10).

As another example, user interface 26 may be configured to accept user settings for high and low limits on $FiO_2$ of the breathing gas delivered to patient 10 that would prevent gas delivery control system 22 from adjusting $FiO_2$ of the breathing gas delivered to patient 10 beyond those limits. The teachings of the present disclosure may provide enhanced safety features in comparison to traditional controllers for gas delivery systems (e.g., reducing the risk of hypoxia resulting from reduced $FiO_2$ of the breathing gas delivered to patient 10 and/or reducing the risk of oxygen toxicity resulting from excess $FiO_2$ of the breathing gas delivered to patient 10 over the long term). The teachings of the present disclosure may be used to control delivery of breathing gas to a patient based on any combination of ventilation parameters and may provide these or additional benefits.

Figure 3:
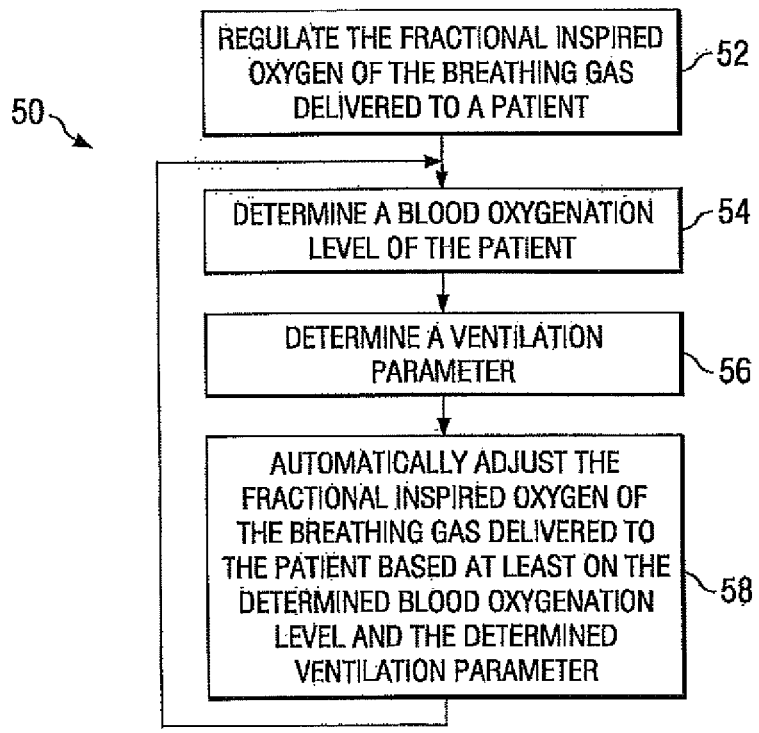
FIG. 3 is a flowchart illustrating a method for controlling the delivery of a breathing gas to a patient using multiple ventilation parameters, according to one embodiment of the present disclosure.

FIG. 3 is a flowchart illustrating a method 50 for controlling the delivery of a breathing gas to a patient based on multiple ventilation parameters in accordance with teachings of the present disclosure. Method 50 may include any steps appropriate for controlling the delivery of breathing gas to a patient based on any two or more ventilation parameters.

At Step 52, breathing assistance system 1 may regulate the $FiO_2$ of the breathing gas delivered to patient 10. For example, gas delivery control system 22 may regulate the $FiO_2$ of the breathing gas delivered to patient 10 by controlling the amount of oxygen let into the stream of breathing gas, e.g., by controlling one or more valves, regulating the pressure, and/or regulating the flow rate of oxygen.

At Step 54, breathing assistance system 1 may determine a blood oxygenation level of patient 10. Breathing assistance system 1 may determine a blood oxygenation level of patient 10, for example, by sensing the patient's $SpO_2$ or any other measurement indicating a blood oxygenation level. As another example, breathing assistance system 1 may receive data from a sensor, a parameter module, a user, and/or any other method for determining a blood oxygenation level.

At Step 56, breathing assistance system 1 may determine another ventilation parameter. As discussed above, a ventilation parameter may include any data relevant and/or related to the delivery of breathing gas to a patient. For example, ventilation parameters may include physiological parameters of the patient, medical history of the patient, equipment-related parameters, historical data related to the delivery of breathing gas, and/or user inputs.

In addition, breathing assistance system 1 may determine another ventilation parameter in any appropriate manner. As an example, breathing assistance system 1 may use sensors configured to collect ventilation parameters, such as sensors associated with patient 10, gas delivery apparatus 20, the surrounding atmosphere, and/or any other data related to patient 10 and/or the operation of gas delivery apparatus 20. As another example, breathing assistance system 1 may be configured to receive data from a user (e.g., a keyboard, a touchpad, and/or any other device described above).

At Step 58, breathing assistance system 1 may automatically adjust the $FiO_2$ of the breathing gas delivered to patient 10 based on the determined blood oxygenation level and the determined ventilation parameter. For example, gas delivery control system 22 may control $FiO_2$ of the breathing gas delivered to patient 10 based on measured $SpO_2$ and at least one physiological parameter, the medical history of the patient, equipment-related parameters, historical data, and/or user inputs.

Breathing assistance system 1 may perform method 50 continuously, periodically, upon a triggering event (e.g., automatically upon detecting a change in one or more particular ventilation parameters), and/or according to any schedule selected by a clinician and/or other user of breathing assistance system 1. For example, breathing assistance system 1 may perform method 50 every 15 seconds, every 5 minutes, every 10 breathing cycles, upon a triggering event (e.g., upon detection of a change in $SpO_2$ or pulse rate), and/or using a combination of schedule and/or triggering events. Breathing assistance system 1 may communicate data related to method 50 to a clinician and/or user through display 30.

Selecting Target Values in a Breathing Assistance System

In operation, breathing assistance system 1 may control $FiO_2$ of the breathing gas delivered to patient 10 based at least on target values for one or more ventilation parameters. For example, breathing assistance system 1 may primarily control the fraction of inspired oxygen ($FiO_2$) in the breathing gas delivered based on a target $SpO_2$ value (e.g., gas delivery control system 22 may adjust the $FiO_2$ by an amount proportional to the difference between a measured $SpO_2$ and a user-specified target $SpO_2$ value). In accordance with the teaching of the present disclosure, breathing assistance system 1 may include user interface 26 and/or display 30 configured to adjust the target values for the one or more ventilation parameters.

Gas delivery control system 22 may include one or more default values for the target values of one or more ventilation parameters. For example, gas delivery control system 22 may be configured to use a default target value for $SpO_2$ and/or end-tidal carbon dioxide ($EtCO_2$), the default target value corresponding to typical values for a healthy human. In some cases, a clinician and/or user of breathing assistance system 1 may prefer to adjust the target values for one or more ventilation parameters. For example, the normal condition of patient 10, however, may vary due to any of several factors (e.g., age, environment, chronic disease, and/or any other relevant health factor). As another example, changes in the patient's disease or treatment course may change the appropriate target value of one or more ventilation parameters.

For example, an infant born prematurely may require a lower $SpO_2$ level than a healthy adult, at least in part because of the risk of Retinopathy of Prematurity. As another example, a patient with severe Chronic Obstructive Pulmonary Disease (COPD) may have a blunted $CO_2$ drive and require a higher $CO_2$ and/or a lower $SpO_2$ level than normal adults. These examples are not intended to be exhaustive, as persons having ordinary skill in the art will be able to identify additional medical conditions and/or treatment protocols that may be improved by implementation of the teachings of the present disclosure.

In systems incorporating the teachings of the present disclosure, adjustment of such target-based treatment protocols may be improved and/or more efficient. User interface 26 and/or display 30 may allow manual adjustment of the target values of one or more ventilation parameters. In some embodiments of the present disclosure, user interface 26 and/or display 30 may allow a user to choose among automated protocols for adjusting a target-based treatment protocol. User interface 26 and/or display 30 may include a touch screen (e.g., a GUI as shown in FIG. 2) and/or additional components configured to accept user input, as discussed with relation to FIG. 1. For example, user interface 26 may include any device for receiving a user input, e.g., a physical interface (a knob, button, dial, etc.), or a button or other interface on a touch screen GUI. In one embodiment, one or more buttons 33 may include a trigger to set the target values for one or more ventilation parameters to a new value (see FIG. 2).

Such changes may be based on clinical assessments of patient 10, historical data related to one or more ventilation parameters, and/or other data related to the condition and/or treatment of patient 10. In some embodiments, breathing assistance system 1 may recommend adjusted target values for one or more ventilation parameters. In other embodiments, breathing assistance system 1 may automatically adjust target values for one or more ventilation parameters. In still other embodiments, breathing assistance system 1 may respond to a user input or trigger to begin a process to adjust target values for one or more ventilation parameters. Some examples of these embodiments are discussed below.

In one embodiment, breathing assistance system 1 may include a selector that sets a target value for a ventilation parameter to the current measured value for that ventilation parameter. The current measured value of a ventilation parameter may be determined in any manner, as more fully discussed with relation to FIG. 1. As one example, user interface 26 may include a selector that sets the target $SpO_2$ value to the current measured $SpO_2$ value determined by parameter module 24. As another example, user interface 26 may include a selector that updates a recommended user-selectable target $SpO_2$ value, either on a periodic basis or subsequent to the occurrence of predetermined events (e.g., after completion of a lung recruitment maneuver or a lung aspiration procedure), based on an analysis of measured $SpO_2$ values determined by parameter module 24.

In another embodiment, breathing assistance system 1 may include a selector that sets a target value for a ventilation parameter to a new value based on a mathematical function of recent measured values for that ventilation parameter. For example, gas delivery control system 22 and/or parameter module 24 may apply a mathematical function to current and/or historical measured values for $SpO_2$ (e.g., average value, maximum value, minimum value, and/or any other mathematical function) to determine and/or set a new target $SpO_2$ value. As another example, gas delivery control system 22 and/or parameter module 24 may apply a mathematical function to the current measured values of two or more ventilation parameters to calculate a target value for one or more ventilation parameters (e.g., $SpO_2$).

In another embodiment, breathing assistance system 1 may include a selector that automatically sets a target value for a ventilation parameter based on a specific disease and/or severity states. For example, gas delivery control system 22 may be preprogrammed with target values for one or more ventilation parameters that correlate to a specific condition (e.g., COPD, premature birth, pneumonia, emphysema, severe COPD, congestive heart failure (CHF), etc.).

In one embodiment, user interface 26 may include one or more selectors labeled and/or identified with a specific condition and gas delivery control system 22 may set a target value for one or more ventilation parameters if a user selects that specific condition. In another embodiment, breathing assistance system 1 may include a selector that sets a target value for a ventilation parameter to a new value based on recommended values determined by gas delivery control system 22 in conjunction with parameter module 24 and/or another information handling system. For example, parameter module 24 may gather data from a hospital information system and use the gathered data to recommend and/or automatically set target values for one or more ventilation parameters.

In another embodiment, breathing assistance system 1 may include a selector that sets a target value for a ventilation parameter to one or more proposed target values preprogrammed for the course of the patient's treatment. For example, gas delivery control system 22 may be preprogrammed with target values for one or more ventilation parameters that correlate to a treatment protocol (e.g., weaning, pre-operative, operating room, PACU, ICU, etc.). For example, the proposed $SpO_2$ target value for a patient during the acute phase of pneumonia in the ICU might be set at 92% to reduce the risk of volutrauma. As another example, the proposed $SpO_2$ target value for a patient that is being weaned from the ventilator during recovery from pneumonia might be set at 96%. As another example, the proposed $SpO_2$ target value for a patient that is undergoing elective surgery with healthy lungs might be set at 98%. In such embodiments, user interface 26 may include one or more options for selecting a treatment protocol (e.g., buttons, dials, touch-screen buttons 33 as shown in FIG. 2, etc.).

In another embodiment, breathing assistance system 1 may include a selector that allows a user to select or specify automatic adjustments in a target value for a ventilation parameter to a new value within a predetermined range, wherein the target value varies as a function of one or more additional ventilation parameters. For example, the oxygen saturation level required to maintain an adequate partial arterial oxygen pressure ($PaO_2$) decreases with increases in body temperature or arterial pH as a result of shifts in the oxygen dissociation curve. Gas delivery control system 22 and/or parameter module 24 may determine a range of appropriate variations in the $SpO_2$ target value based on changes in the patient's core temperature or blood pH level to compensate for these shifts in the oxyhemoglobin dissociation curve.

Figure 4:
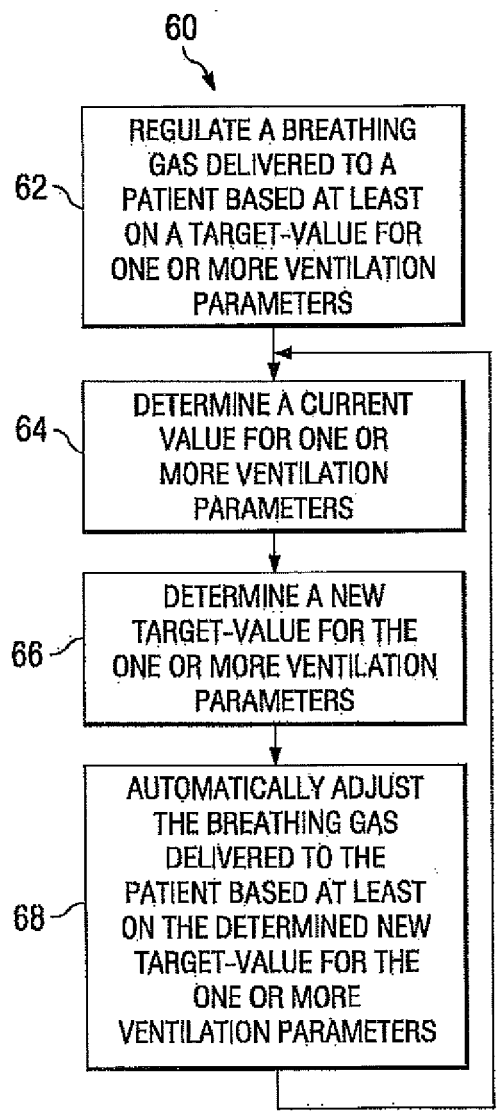
FIG. 4 is a flowchart illustrating a method for controlling the delivery of a breathing gas to a patient including selecting the target value for one or more ventilation parameters in a breathing assistance device, according to another embodiment of the present disclosure.

FIG. 4 is a flowchart illustrating a method 60 for controlling the delivery of a breathing gas to a patient by selecting target values for ventilation parameters in accordance with teachings of the present disclosure. Method 60 may include any steps appropriate for selecting the target value for one or more ventilation parameters in a breathing assistance device. As discussed above, a ventilation parameter may include any data relevant and/or related to the delivery of breathing gas to a patient. For example, ventilation parameters may include physiological parameters of the patient, medical history of the patient, equipment-related parameters, historical data related to the delivery of breathing gas, and/or user inputs.

At Step 62, breathing assistance system 1 may regulate a breathing gas delivered to patient 10 based on a target value for one or more ventilation parameters. For example, gas delivery control system 22 may regulate the pressure and/or flow of gas delivered to patient 10. As another example, gas delivery control system 22 may regulate the $FiO_2$ of the breathing gas delivered to patient 10 by controlling the amount of oxygen let into the stream of breathing gas. In some embodiments, gas delivery control system 22 may regulate the $FiO_2$ of the breathing gas delivered to patient 10 based on a target value for the patient's $SpO_2$.

At Step 64, breathing assistance system 1 may determine a current value for the one or more ventilation parameters (e.g., a blood oxygenation level of patient 10). For example, parameter module 24 may determine a blood oxygenation level of patient 10, for example, by sensing the patient's $SpO_2$ or any other measurement indicating a blood oxygenation level. As another example, parameter module 24 may receive data from a sensor, a parameter module, a user, and/or any other method for determining a ventilation parameter.

At Step 66, breathing assistance system 1 may determine new target values for the one or more ventilation parameters. For example, breathing assistance system 1 may determine new target values for one or more ventilation parameters based on the analysis of current or historical measured values for the one or more ventilation parameters (e.g., by calculating an average value for one or more ventilation parameters and/or determining a maximum and/or minimum value for the one or more ventilation parameters). As another example, breathing assistance system 1 may determine new target values for one or more ventilation parameters based on the analysis of the patient's disease state, treatment course, and/or medical history.

The determination of new target values for the one or more ventilation parameters may be responsive to a user input, a pre-programmed event, and/or the analysis of one or more ventilation parameters. For example, a user may press one or more buttons 33 associated with display 30 to initiate the determination. As another example, display 30 may display a message, alert, alarm, and/or another indication that a new target value may be appropriate. Display 30 may display a history of prior target values and/or measured values for one or more ventilation parameters and/or any other data that may be useful for a clinician or user to decide whether to change the target values of one or more ventilation parameters.

At Step 68, breathing assistance system 1 may automatically adjust the breathing gas delivered to patient 10 based on the determined new target values for the one or more ventilation parameters. For example, gas delivery control system 22 may control $FiO_2$ of the breathing gas delivered to patient 10 based on the new determined target value for $SpO_2$ determined at Step 66.

Breathing assistance system 1 may perform method 60 continuously, periodically, upon a triggering event (e.g., automatically upon detecting a change in one or more particular ventilation parameters), and/or according to any schedule selected by a clinician, and/or other user of breathing assistance system 1. For example, breathing assistance system 1 may perform method 60 every 15 seconds, every 5 minutes, once 10 breathing cycles, upon a triggering event (e.g., detection of a change in $SpO_2$ or pulse rate), and/or using a combination of schedule and/or triggering events.

Automatic Lung Recruitment Maneuvers

Lung recruitment maneuvers may be useful in the treatment of patients with certain disease states that may impair oxygen diffusion (e.g., those that involve atalectasis and/or inflammation). For example, patients with pneumonia, respiratory distress syndrome (RDS), acute lung injury (ALI), acute respiratory distress syndrome (ARDS), infant respiratory distress syndrome (IRDS), and/or various injuries to the lung, may exhibit reduced ability to absorb oxygen from air and/or other breathing gas into the lung. In some cases, these conditions are the result of collapsed and/or occluded alveoli in the lung A lung recruitment maneuver typically consists of providing a breathing gas to patient 10 at a relatively high pressure for enough time to distend collapsed alveoli (e.g., 40 cm water for 40 seconds). Repeated lung recruitment maneuvers, however, may increase the risk of volutrauma and/or barotrauma.

In accordance with teachings of the present disclosure, breathing assistance system 1 may combine controlling the delivery of breathing gas to patient 10 based on one or more ventilation parameters with automatically recommending and/or providing lung recruitment maneuvers. In addition, after a lung recruitment maneuver is completed, breathing assistance system 1 may control PEEP (or another ventilation parameter) to reduce the chance of a new collapse/occlusion and the resulting need for another lung recruitment maneuver.

In one embodiment, breathing assistance system 1 may trigger and/or recommend a lung recruitment maneuver based on a measure of oxygen diffusion across the lung (e.g., the relationship between blood oxygen content (e.g., $SpO_2$ or $PaO_2$) and gas oxygen content (e.g., $FiO_2$ or $PAO_2$)). In embodiments that regulate the $FiO_2$ of breathing gas delivered to patient 10 based on a target value for $SpO_2$, changes in the $FiO_2$ level may indicate changes in the oxygen diffusion capacity of the patient's lungs, indicating the need for a lung recruitment maneuver. For example, breathing assistance system 1 may trigger and/or recommend a lung recruitment maneuver if the $FiO_2$ level exceeds a predetermined threshold (e.g., set by breathing assistance system 1 or a clinician). In one specific example, breathing assistance system 1 may trigger a lung recruitment maneuver if patient 10 requires over 60% $FiO_2$ to maintain $SpO_2$ over 90%. In some embodiments, gas delivery control system 22 may eliminate, restrict, and/or otherwise inhibit changes in delivery of breathing gas to patient 10 (e.g., inhibit the change of $FiO_2$ in the breathing gas delivered to patient 10 based on the target value of $SpO_2$) while the lung recruitment maneuver is underway.

A lung recruitment maneuver may deliver breathing gas at any pressure and/or duration appropriate for the treatment of patient 10. The pressure and/or duration may be default values stored by gas delivery control system 22, user input determined by a clinician and/or another user, and/or determined automatically by delivery control system 22 based on the severity of the patient's condition. These factors may be automatically modified and/or adjusted by gas delivery control system 22 based on one or more ventilation parameters (e.g., time since the last lung recruitment maneuver, rate of recent $FiO_2$ increases during previous lung recruitment maneuvers, and/or the extent to which $SpO_2$ remains below its target value despite $FiO_2$ increases).

In some embodiments, after performing a lung recruitment maneuver, breathing assistance system 1 may automatically adjust the settings of one or more ventilation parameters related to the delivery of breathing gas (e.g., pressure, flow rate, PEEP, etc.). For example, after performing a lung recruitment maneuver, breathing assistance system 1 may automatically change the target values of one or more ventilation parameters (e.g., $SpO_2$). In one specific embodiment, breathing assistance system 1 may adjust a PEEP setting for the breathing gas delivered to patient 10 so that post-maneuver PEEP starts at 20 cm water and reduces in 2 cm increments every few minutes as long as $SpO_2$ remains above 94%. In another specific embodiment, the post-maneuver PEEP may start at a level determined by one or more ventilation parameters (e.g., the time elapsed since the previous lung recruitment maneuver). Maintaining an elevated PEEP level may maintain lung recruitment longer than returning to the original PEEP level used in the delivery of breathing gas to patient 10. In addition, later reductions in PEEP may limit the risk of barotrauma.

After automatically adjusting the settings of the one or more ventilation parameters, breathing assistance system 1 may later automatically adjust the setting of the one or more ventilation parameters consistent with the variation of one or more other ventilation parameters. For example, if breathing assistance system 1 has automatically adjusted the PEEP setting to maintain lung recruitment, it may slowly reduce the PEEP setting going forward. In such embodiments, breathing assistance system 1 may adjust PEEP using a slower response time than adjustments to $FiO_2$ so that $FiO_2$ settings may reach equilibrium before any change to the PEEP setting. For example, breathing assistance system 1 may adjust the $FiO_2$ setting every 30 seconds, if needed, but adjust the PEEP settings every 2-5 minutes, if needed. In addition, breathing assistance system 1 may prevent PEEP adjustments as long as $FiO_2$ remains above a certain threshold. In another embodiment, breathing assistance system 1 may adjust PEEP settings based on a combination of $FiO_2$ settings and one or more ventilation parameters (e.g., time elapsed between recruitment maneuvers, pulse rate and/or blood pressure), for example, balancing the benefits of increased alveolar recruitment with reduced central venous return flow.

As another example, breathing assistance system 1 may automatically adjust PEEP both upward and downward after a lung recruitment maneuver. One benefit of bidirectional adjustments may be maintaining $FiO_2$ at a pre-determined target value that indicates satisfactory oxygen diffusion and remains below the $FiO_2$ threshold for recommending and/or triggering a subsequent lung recruitment maneuver. The magnitude and/or frequency of such adjustments may be fixed, adjusted by a user and/or clinician, and/or calculated by gas delivery control system 22 based on one or more ventilation parameters. As examples, the adjustments may depend on current $FiO_2$, the rate of change of $FiO_2$, and/or the relationship between $SpO_2$ values and the $SpO_2$ target. In one specific example, if the PEEP level is close to a pre-determined maximum allowed value, downward PEEP adjustments might become larger and/or more frequent than upward adjustments.

Figure 5:
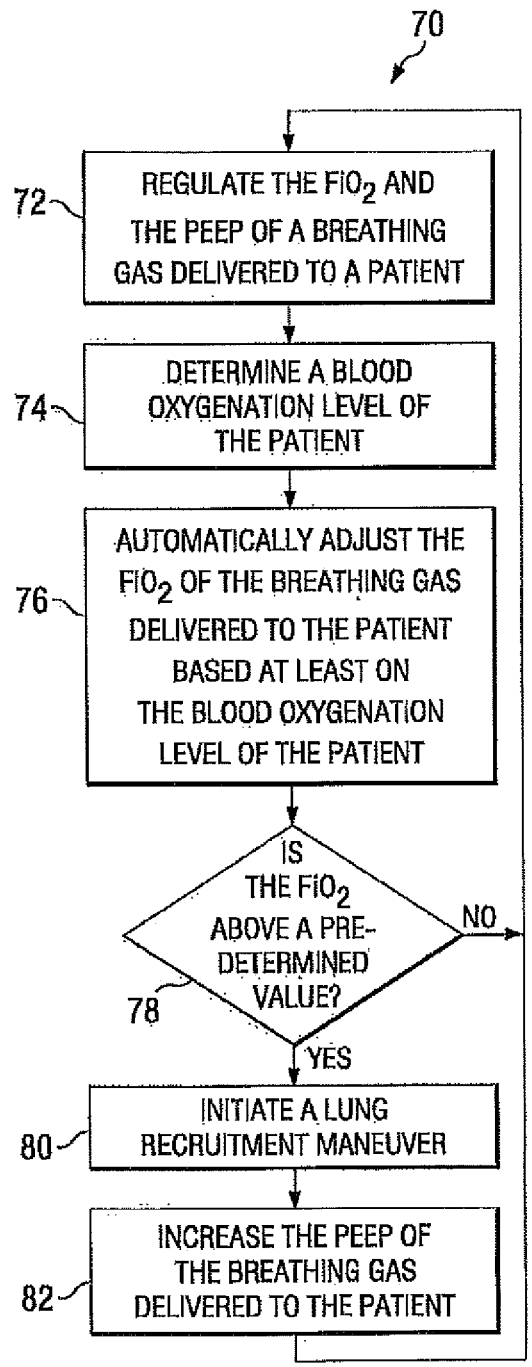
FIG. 5 is a flowchart illustrating a method for controlling the delivery of a breathing gas to a patient including automatic lung recruitment maneuvers, according to another embodiment of the present disclosure.

FIG. 5 is a flowchart illustrating a method 70 for controlling the delivery of a breathing gas to a patient, including performing automatic lung recruitment maneuvers, according to one embodiment of the present disclosure. Method 70 may include any steps appropriate for initiating a lung recruitment maneuver based on one or more ventilation parameters, including managing post recruitment PEEP settings to reduce the chance of subsequent lung recruitment maneuvers. As discussed above, a ventilation parameter may include any data relevant and/or related to the delivery of breathing gas to a patient. For example, ventilation parameters may include physiological parameters of the patient, medical history of the patient, equipment-related parameters, historical data related to the delivery of breathing gas, and/or user inputs.

At Step 72, breathing assistance system 1 may regulate the $FiO_2$ and PEEP of a breathing gas delivered to patient 10. In other embodiments, breathing assistance system 1 may regulate alternative and/or additional ventilation parameters (e.g., inspired pressure, tidal volume, I:E ratio, and/or mandatory breath rate).

At Step 74, breathing assistance system 1 may determine a blood oxygenation level (e.g., $SpO_2$) of patient 10. Additionally or alternatively, breathing assistance system 1 may determine a value for one or more ventilation parameters (e.g., indications of the diffusion capacity of the patient's lungs). The determination may be performed by parameter module 24 and/or any other components of breathing assistance system 1, e.g., as described with reference to FIG. 1.

At Step 76, breathing assistance system 1 may automatically adjust the $FiO_2$ of the breathing gas delivered to patient 10 based on at least the determined blood oxygenation level of patient 10. Additionally or alternatively, breathing assistance system 1 may automatically adjust one or more ventilation parameters (inspired pressure, tidal volume, I:E ratio, and/or mandatory breath rate) based on at least the determined value of one or more ventilation parameters (e.g., pulse and/or blood pressure). For example, breathing assistance system 1 may control $FiO_2$ of the breathing gas delivered to patient 10 based on the difference between the determined blood oxygenation level of patient 10 and a target value for $SpO_2$.

At Step 78, breathing assistance system 1 may determine whether the $FiO_2$ setting is above a predetermined value. In embodiments regulating different and/or additional ventilation parameters, breathing assistance system 1 may determine whether another particular controlled parameter is above or below a pre-determined value. For example, gas delivery control system 22 may determine whether the $FiO_2$ setting is above 60%. If not, method 70 may return to Step 72.

At Step 80, if breathing assistance system 1 has determined that the $FiO_2$ setting (or the setting for another controlled ventilation parameter) has crossed a pre-determined threshold, gas delivery control system 22 may initiate a lung recruitment maneuver At Step 82, after a lung recruitment maneuver is complete, breathing assistance system 1 may control one or more PEEP settings of the breathing gas delivered to patient 10 to reduce the chances of a subsequent lung recruitment maneuver. Once Step 82 is complete, method 70 may return to Step 72.

Breathing assistance system 1 may perform method 70 continuously, periodically, upon a triggering event (e.g., automatically upon detecting a change in one or more ventilation parameters), and/or according to any schedule selected by a clinician and/or other user of breathing assistance system 1. For example, breathing assistance system 1 may perform method 60 every 15 seconds, every 5 minutes, once every 10 breathing cycles, upon a triggering event (e.g., each time $FiO_2$ is adjusted), and/or using a combination of schedule and/or triggering events.

It will be appreciated that while the disclosure is particularly described in the context of breathing assistance systems, the apparatuses, techniques, and methods disclosed herein may be similarly applied in other contexts. Additionally, it should be understood that various changes, substitutions and alterations can be made herein without departing from the spirit and scope of the disclosure as illustrated by the following claims.

What is claimed is:

1. A method for controlling a delivery of a breathing gas to a patient using a processor, the method including:
   regulating a fractional inspired oxygen ($FiO_2$) and a positive end expiratory pressure (PEEP) of the breathing gas delivered to the patient;
   determining a blood oxygenation level of the patient;
   automatically adjusting the $FiO_2$ of the breathing gas delivered to the patient based on the blood oxygenation level of the patient; and
   in response to determining that the $FiO_2$ of the breathing gas delivered to the patient exceeds a pre-determined value:
      automatically initiating a lung recruitment maneuver to achieve a lung recruitment;

after completion of the lung recruitment maneuver:
   setting a post-recruitment maneuver PEEP at a higher level than a PEEP level setting prior to the lung recruitment maneuver;
   periodically determining, at a first specified frequency, whether to adjust the $FiO_2$ of the delivered breathing gas; and
   periodically determining, at a second specified frequency, whether to reduce the PEEP;
   wherein the second defined frequency of PEEP reduction determinations is lower than the first defined frequency of $FiO_2$ adjustment determinations such that the $FiO_2$ is allowed to reach equilibrium between successive PEEP reduction determinations.

2. The method of claim 1, wherein the blood oxygenation level is determined by measuring saturation of peripheral oxygen ($SpO_2$) in the patient.

3. The method of claim 1, wherein the lung recruitment maneuver includes:
   inflating lungs of the patient at a relatively high pressure; and
   maintaining the inflation of the lungs for a duration long enough to distend collapsed aveoli.

4. The method of claim 1, wherein the lung recruitment maneuver includes:
   inflating lungs of the patient at a relatively high pressure, the pressure preset by a user; and
   maintaining the inflation of the lungs for a duration long enough to distend collapsed aveoli, the duration preset by the user.

5. The method of claim 1, wherein the lung recruitment maneuver includes:
   inflating lungs of the patient at a relatively high pressure, the pressure determined by a ventilation parameter; and
   maintaining the inflation of the lungs for a duration long enough to distend collapsed aveoli, the duration determined by the ventilation parameter.

6. The method of claim 1, further comprising inhibiting the adjustment of the fractional inspired oxygen of the breathing gas delivered to the patient during the lung recruitment maneuver.

7. The method of claim 1, wherein maintaining a duration of the lung recruitment after completion of the lung recruitment maneuver comprises automatically adjusting the PEEP of the breathing gas delivered to the patient based on variations in the fractional inspired oxygen of the breathing gas delivered to the patient.

8. The method of claim 1, wherein maintaining a duration of the lung recruitment after completion of the lung recruitment maneuver comprises automatically adjusting the PEEP of the breathing gas delivered to the patient based on both:
   variations in the $FiO_2$ of the breathing gas delivered to the patient; and
   a ventilation parameter including one cardiovascular indicator of the patient.

9. The method of claim 1, further comprising:
   regulating a third gas delivery parameter of the breathing gas delivered to the patient;
   automatically adjusting the third gas delivery parameter of the breathing gas delivered to the patient based on the blood oxygenation level of the patient; and
   adjusting the pre-determined value for automatic initiation of the lung recruitment maneuver based on the value of the third gas delivery parameter of the breathing gas delivered to the patient.

10. A breathing assistance system configured to deliver a breathing gas toward a patient, the system comprising:
   a gas delivery control system configured to regulate a fractional inspired oxygen ($FiO_2$) and a positive end expiratory pressure (PEEP) of the breathing gas delivered to the patient;
   a parameter module configured to determine a blood oxygenation level of the patient;
   wherein the gas delivery control system:
      automatically adjusts the $FiO_2$ of the breathing gas delivered to the patient based at least on the blood oxygenation level of the patient;
      automatically initiates a lung recruitment maneuver to achieve a lung recruitment when the $FiO_2$ of the breathing gas exceeds a pre-determined value; and
      after completion of the lung recruitment maneuver:
         sets a post-recruitment maneuver PEEP at a higher level than a PEEP level setting prior to the lung recruitment maneuver;
         periodically determines, at a first specified frequency, whether to adjust the $FiO_2$ of the delivered breathing gas; and
         periodically determines, at a second specified frequency, whether to reduce the PEEP;
         wherein the second defined frequency of PEEP reduction determinations is lower than the first defined frequency of $FiO_2$ adjustment determinations such that the $FiO_2$ is allowed to reach equilibrium between successive PEEP reduction determinations.

11. The system of claim 10, wherein the parameter module is configured to measure saturation of peripheral oxygen ($SpO_2$) in the patient.

12. The system of claim 10, wherein the lung recruitment maneuver includes:
   inflating lungs of the patient at a relatively high pressure; and
   maintaining the inflation of the lungs for a duration long enough to distend collapsed aveoli.

13. The system of claim 10, wherein the lung recruitment maneuver includes:
   inflating lungs of the patient at a relatively high pressure, the pressure preset by a user; and
   maintaining the inflation of the lungs for a duration long enough to distend collapsed aveoli, the duration preset by the user.

14. The system of claim 10, wherein the lung recruitment maneuver includes:
   inflating lungs of the patient at a relatively high pressure, the pressure determined by a ventilation parameter; and
   maintaining the inflation of the lungs for a duration long enough to distend collapsed aveoli, the duration determined by the ventilation parameter.

15. The system of claim 10, further comprising the gas delivery control system configured to inhibit the adjustment of the $FiO_2$ of the breathing gas delivered to the patient during the lung recruitment maneuver.

16. The system of claim 10, wherein maintaining a duration of the lung recruitment after completion of the lung recruitment maneuver comprises automatically adjusting the PEEP of the breathing gas delivered to the patient based on variations in the $FiO_2$ of the breathing gas delivered to the patient.

17. The system of claim 10, wherein maintaining a duration of the lung recruitment after completion of the lung recruitment maneuver comprises automatically adjusting the PEEP of the breathing gas delivered to the patient based on both:

variations in the $FiO_2$ of the breathing gas delivered to the patient; and a ventilation parameter including one cardiovascular indicator of the patient.

18. The system of claim 10, further comprising:

the gas delivery control system configured to regulate a third parameter of the breathing gas delivered to the patient;

the gas delivery control system configured to automatically adjust the third parameter of the breathing gas delivered to the patient based on the blood oxygenation level of the patient; and the gas delivery control system configured to adjust the pre-determined value for automatic initiation of the lung recruitment maneuver based on the value of the third parameter of the breathing gas delivered to the patient.

19. A computer-readable storage medium storing a set of instructions executable on a processor, the set of instructions comprising:

instructions for regulating a fractional inspired oxygen ($FiO_2$) and a positive end expiratory pressure (PEEP) of a breathing gas delivered to a patient;

instructions for determining a blood oxygenation level of the patient;

instructions for automatically adjusting the $FiO_2$ of the breathing gas delivered to the patient based on the blood oxygenation level of the patient; and instructions for, in response to determining that the $FiO_2$ of the breathing gas delivered to the patient exceeds a pre-determined value:

automatically initiating a lung recruitment maneuver to achieve a lung recruitment; and after completion of the lung recruitment maneuver:

setting a post-recruitment maneuver PEEP at a higher level than a PEEP level setting prior to the lung recruitment maneuver;

periodically determining, at a first specified frequency, whether to adjust the $FiO_2$ of the delivered breathing gas; and periodically determining, at a second specified frequency, whether to reduce the PEEP;

wherein the second defined frequency of PEEP reduction determinations is lower than the first defined frequency of $FiO_2$ adjustment determinations such that the $FiO_2$ is allowed to reach equilibrium between successive PEEP reduction determinations.

20. A breathing assistance system, comprising:

means for regulating a fractional inspired oxygen ($FiO_2$) and a positive end expiratory pressure (PEEP) of a breathing gas delivered to a patient;

means for determining a blood oxygenation level of the patient;

means for automatically adjusting the $FiO_2$ of the breathing gas delivered to the patient based on the blood oxygenation level of the patient; and means for, in response to determining that the $FiO_2$ of the breathing gas delivered to the patient exceeds a pre-determined value:

automatically initiating a lung recruitment maneuver to achieve a lung recruitment;

after completion of the lung recruitment maneuver:

setting a post-recruitment maneuver PEEP at a higher level than a PEEP level setting prior to the lung recruitment maneuver;

periodically determining, at a first specified frequency, whether to adjust the $FiO_2$ of the delivered breathing gas; and periodically determining, at a second specified frequency, whether to reduce the PEEP;

wherein the second defined frequency of PEEP reduction determinations is lower than the first defined frequency of determinations such that the $FiO_2$ is allowed to reach equilibrium between successive PEEP reduction determinations.

* * * * *